(12) United States Patent
Sharma

(10) Patent No.: US 10,929,973 B2
(45) Date of Patent: Feb. 23, 2021

(54) MEDICAL IMAGE PRE-PROCESSING AT THE SCANNER FOR FACILITATING JOINT INTERPRETATION BY RADIOLOGISTS AND ARTIFICIAL INTELLIGENCE ALGORITHMS

(71) Applicant: Siemens Healthcare GmbH, Erlangen (DE)

(72) Inventor: Puneet Sharma, Princeton Junction, NJ (US)

(73) Assignee: Siemens Healtcare GmbH, Erlangen (DE)

(*) Notice: Subject to any disclaimer, the term of this patent is extended or adjusted under 35 U.S.C. 154(b) by 165 days.

(21) Appl. No.: 16/149,226

(22) Filed: Oct. 2, 2018

(65) Prior Publication Data
US 2020/0104994 A1    Apr. 2, 2020

(51) Int. Cl.
*G06T 7/00* (2017.01)
*G16H 30/40* (2018.01)
(Continued)

(52) U.S. Cl.
CPC .......... *G06T 7/0012* (2013.01); *A61B 6/5205* (2013.01); *G16H 30/40* (2018.01);
(Continued)

(58) Field of Classification Search
CPC . G06T 2207/30004; G06T 2207/20081; G06T 7/0012; G16H 50/20; G16H 30/40; A61B 6/5205
See application file for complete search history.

(56) References Cited

U.S. PATENT DOCUMENTS 8,724,871 B1 * 5/2014 Biagiotti ............... G06T 7/0014
                                                          382/128
8,787,638 B2 * 7/2014 Zee ......................... A61B 3/12
                                                          382/128
(Continued)

FOREIGN PATENT DOCUMENTS

WO    WO2018015414 A1    1/2018

OTHER PUBLICATIONS

Extended European Search Report (EESR) dated Feb. 14, 2020 in corresponding European Patent Application No. 19200348.1.
(Continued)

*Primary Examiner* — Mia M Thomas

(57) ABSTRACT

A method and system for medical image pre-processing at the medical image scanner that facilitates joint interpretation of the medical images by radiologists and artificial intelligence algorithms is disclosed. Raw medical image data is acquired by performing a medical image scan of a patient using a medical image scanner. Input data associated with the medical image scan of the patient and available downstream automated image analysis algorithms is acquired. A set of pre-processing algorithms to apply to the raw medical image data is selected based on the input data associated with the medical image scan of the patient and the available downstream automated image analysis algorithms using a trained machine learning based model. One or more medical images are generated from the raw medical image data by applying the selected set of pre-processing algorithms to the raw medical image data.

14 Claims, 4 Drawing Sheets

(51) Int. Cl.
*A61B 6/00* (2006.01)
*G16H 50/20* (2018.01)

(52) U.S. Cl.
CPC .............. *G06T 2207/20081* (2013.01); *G06T 2207/30004* (2013.01); *G16H 50/20* (2018.01)

(56) References Cited

U.S. PATENT DOCUMENTS

| | | | | |
|---|---|---|---|---|
| 9,177,102 | B2* | 11/2015 | Bower | G16H 30/20 |
| 9,519,753 | B1 | 12/2016 | Gerdeman et al. | |
| 9,757,588 | B2* | 9/2017 | Kaus | G06T 7/38 |
| 10,165,987 | B2* | 1/2019 | Cales | A61B 5/0095 |
| 10,463,336 | B2* | 11/2019 | Itu | G06K 9/6262 |
| 10,803,612 | B2* | 10/2020 | Langeland | G06T 7/70 |
| 10,824,857 | B2* | 11/2020 | Flohr | G06N 20/00 |
| 2007/0211929 | A1* | 9/2007 | Beddoe | G06T 7/0012 |
| | | | | 382/128 |
| 2007/0237380 | A1* | 10/2007 | Iwase | A61B 6/032 |
| | | | | 382/131 |
| 2012/0275677 | A1* | 11/2012 | Bower | G06T 7/0012 |
| | | | | 382/131 |
| 2013/0195331 | A1* | 8/2013 | Yi | G06F 19/321 |
| | | | | 382/128 |
| 2013/0301889 | A1* | 11/2013 | Abramoff | G06K 9/00 |
| | | | | 382/128 |
| 2014/0276030 | A1* | 9/2014 | McCollough | G06F 19/328 |
| | | | | 600/430 |
| 2015/0104090 | A1* | 4/2015 | Hopfgartner | A61B 8/0891 |
| | | | | 382/131 |
| 2015/0379708 | A1* | 12/2015 | Abramoff | G06K 9/6276 |
| | | | | 382/128 |
| 2016/0335779 | A1* | 11/2016 | Satish | G06T 7/62 |
| 2016/0350480 | A1* | 12/2016 | Gerdeman | G16H 30/20 |
| 2017/0258433 | A1* | 9/2017 | Gulsun | G06T 13/20 |
| 2018/0313925 | A1* | 11/2018 | Parker | G01R 33/56341 |
| 2019/0336096 | A1* | 11/2019 | Itu | A61B 34/10 |
| 2019/0385283 | A1* | 12/2019 | McCloskey | G06K 9/40 |
| 2020/0160973 | A1* | 5/2020 | Andersen | G16H 30/40 |
| 2020/0176112 | A1* | 6/2020 | Sati | G16H 15/00 |

OTHER PUBLICATIONS

Jonas Adler et al: "Task adapted reconstruction for inverse problems"; Aug. 27, 2018; Arxiv. Org.; Cornell University Library; 201 Olin Library Cornell University Ithaca; NY 14853.

Dufan, Wu et al; "End-to-end abnormality detection in medical imaging." Nov. 6, 2017; arXiv preprint arXiv:1711.02074 (2017).; Cornell University Library; pp. 1-15.

* cited by examiner

MEDICAL IMAGE PRE-PROCESSING AT THE SCANNER FOR FACILITATING JOINT INTERPRETATION BY RADIOLOGISTS AND ARTIFICIAL INTELLIGENCE ALGORITHMS

BACKGROUND OF THE INVENTION

The present invention relates to pre-processing medical image data at the medical image scanner used to acquire the medical image data, and more particularly to medical image pre-processing at the medical image scanner to facilitate joint interpretation of the medical images by radiologists and artificial intelligence algorithms.

Various artificial intelligence (AI) based image analysis algorithms are being introduced at a rapid pace for assisting the radiology reading and reporting workflow. These algorithms are trained on retrospectively collected medical images, which were all generated by applying a "pre-processing" algorithm to the raw data acquired by a medical image scanner (e.g., computed tomography (CT) scanner, magnetic resonance (MR) scanner, ultrasound scanner, positron emission tomography (PET) scanner, etc.) for the primary purpose of generating medical images to be visually analyzed by a radiologist. As a result, a large amount of information in the raw medical image data is not being utilized for training the AI algorithms. In addition, the pre-processing algorithms are applied at the scanner without knowledge of the downstream workflow, i.e., will a radiologist read the images with or without the help of an AI system, and if so, what kind of algorithm will be used for the interpretation?

In order to generate medical images, medical image scanners scan patients to acquire raw data and a pre-processing algorithm is applied to the raw data to reconstruct 2D or 3D medical images from the raw data. In current practice, image reconstruction is performed for the main purpose of creating human interpretable images that can then be analyzed by a radiologist. In certain instances multiple instances of reconstruction are performed, each using a different set of parameters. In addition, other image pre-processing algorithms, such as filtering, de-noising, etc., are also performed to aid in visual interpretation of images by humans. However, none of these pre-processing algorithms are informed on the downstream workflow for the resulting medical images.

BRIEF SUMMARY OF THE INVENTION

The present invention provides a method and system for computer-based medical image pre-processing that is automatically tailored based on the downstream tasks to be performed on the acquired medical image data.

In an embodiment of the present invention, a method for medical image acquisition and pre-processing comprises: acquiring raw medical image data by performing a medical image scan of a patient using a medical image scanner; acquiring input data associated with the medical image scan of the patient and available downstream automated image analysis algorithms; selecting a set of pre-processing algorithms to apply to the raw medical image data based on the input data associated with the medical image scan of the patient and the available downstream automated image analysis algorithms using a trained machine learning based model; and generating one or more medical images from the raw medical image data by applying the selected set of pre-processing algorithms to the raw medical image data.

In an embodiment, selecting a set of pre-processing algorithms to apply to the raw medical image data based on the input data associated with the medical image scan of the patient and the available downstream automated image analysis algorithms using a trained machine learning based model comprises: selecting a first set of one or more pre-processing algorithms for generating one or medical images for human visual interpretation; and selecting a second set of one or more pre-processing algorithms for generating one or more medical images for automated image analysis using one or more of the available downstream automated image analysis algorithms.

In an embodiment, generating one or more medical images from the raw medical image data by applying the selected set of pre-processing algorithms to the raw medical image data comprises: generating one or more medical images for human visual interpretation by applying the first set of one or more pre-processing algorithms to the raw medical image data; and generating one or more medical images for automated image analysis by applying the second set of pre-processing algorithms to the raw medical image data.

In an embodiment, the method further comprises: displaying the one or more medical images for human visual interpretation generated using the first set of pre-processing algorithms on a display device; and providing the one or more medical images for automated image analysis generating using the second set of pre-processing algorithms as input to one or more of the available downstream automated image analysis algorithms.

In an embodiment, the method further comprises: displaying results of the automated image analysis performed on the one or more medical images generated using the second set of pre-processing algorithms by the one or more of the available downstream automated image analysis algorithms on the one or more medical images generated using the first set of pre-processing algorithms.

In an embodiment, the first set of pre-processing algorithms and the second set of pre-processing algorithms include reconstruction algorithms with different settings.

In an embodiment, the second set of pre-processing algorithms includes one or more pre-processing algorithms corresponding to each of a plurality of available downstream automated image analysis algorithms predicted to be applied to the medical image scan, and generating one or more medical images for automated image analysis by applying the second set of pre-processing algorithms to the raw medical image data comprises: generating a respective medical image suited for each of the plurality available downstream automated image analysis algorithms predicted to be applied to the medical image scan using the corresponding one or more pre-processing algorithms in the second set of pre-processing algorithms.

In an embodiment, the trained machine learning based model is trained based on a training database of training images acquired using a variety of pre-processing algorithms by comparing output interpretations of the training images determined using one or more available downstream automated image processing algorithms with ground truth interpretations of the training images.

In an embodiment of the present invention, an apparatus for medical image acquisition and pre-processing comprises: means for acquiring raw medical image data by performing a medical image scan of a patient using a medical image scanner; means for acquiring input data associated with the medical image scan of the patient and available downstream automated image analysis algorithms;

means for selecting a set of pre-processing algorithms to apply to the raw medical image data based on the input data associated with the medical image scan of the patient and the available downstream automated image analysis algorithms using a trained machine learning based model; and means for generating one or more medical images from the raw medical image data by applying the selected set of pre-processing algorithms to the raw medical image data.

In an embodiment of the present invention, a non-transitory computer readable medium stores computer program instructions for medical image acquisition and pre-processing. The computer program instructions, when executed by a processor, cause the processor to perform operations comprising: acquiring raw medical image data by controlling a medical image scanner to perform a medical image scan of a patient; acquiring input data associated with the medical image scan of the patient and available downstream automated image analysis algorithms; selecting a set of pre-processing algorithms to apply to the raw medical image data based on the input data associated with the medical image scan of the patient and the available downstream automated image analysis algorithms using a trained machine learning based model; and generating one or more medical images from the raw medical image data by applying the selected set of pre-processing algorithms to the raw medical image data.

These and other advantages of the invention will be apparent to those of ordinary skill in the art by reference to the following detailed description and the accompanying drawings.

DETAILED DESCRIPTION

The present invention relates to medical image pre-processing at the medical image scanner to facilitate joint interpretation of the medical images by radiologists and artificial intelligence algorithms. Embodiments of the present invention provide a method and system for computer-based medical image pre-processing that is automatically tailored based on the downstream tasks to be performed on the acquired medical image data. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system or a remote computer system.

In one embodiment of the present invention, medical image pre-processing may refer to the task of image reconstruction, which converts the raw acquired data from a medical image scanner into a human perceptible medical image. In other embodiment, the pre-processing may also refer to image filtering, denoising, enhancement, and/or other types of medical image pre-processing algorithms.

In current practice, the pre-processing step is performed for the main purpose of creating human interpretable images that can then be analyzed by a radiologist. The downstream analysis task performed by the radiologist may be completely manual (i.e., visually observing the patterns in the image and classifying them as medical findings), or semi-automated (i.e., employing image processing tools and algorithms). However, the pre-processing step is not informed on the downstream analysis tasks to be performed on the resulting medical images. Embodiments of the present automatically tailor the pre-processing algorithms based on the downstream tasks to be performed on the acquired medical image data, which provides benefits of generating medical images that are more suited to the specific analysis tasks to be performed and facilitating joint interpretation of the medical images by radiologists and artificial intelligence algorithms.

Figure 1:
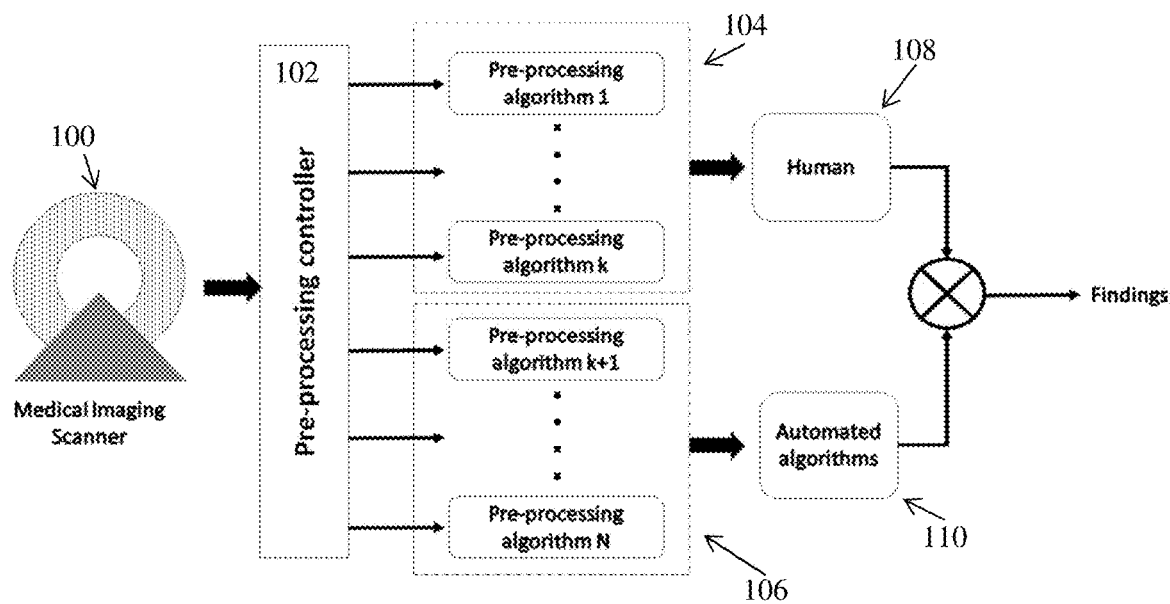
FIG. 1 illustrates a system or performing medical image pre-processing and a pre-processing pipeline according to an embodiment of the present invention.

FIG. 1 illustrates a system or performing medical image pre-processing and a pre-processing pipeline according to an embodiment of the present invention. As shown in FIG. 1, the system includes a medical imaging scanner 100 and a pre-processing controller 102. The medical imaging scanner 100 scans a patient and acquired raw medical image data from the scan. The medical imaging scanner 100 can be a computed tomography (CT) scanner, magnetic resonance (MR) scanner, ultrasound scanner, positron emission tomography (PET) scanner, or any other type of scanner used corresponding to a medical imaging modality. Depending on the type of medical imaging modality, the raw medical image data can be in the form of projection images (e.g., CT), k-space data (in MR), acoustic data (ultrasound), sonograms, etc. The raw medical data acquired by the medical imaging scanner 100 is pre-processed by a number of pre-processing algorithms including a first set of pre-processing algorithms 104 (pre-processing algorithm 1—pre-processing algorithm k) which produce medical images for visual interpretation by humans (e.g., radiologists), while a second set of pre-processing algorithms 106 (pre-processing algorithm k+1—pre-processing algorithm N) generate medical images that are exclusively meant for being processed by automated image analysis algorithms.

The pre-processing controller 102 determines which particular pre-processing algorithms should be executed and with which parameters for a particular scan. The pre-processing controller 102 is implemented one a computer system incorporated within or connected to the medical imaging scanner 100. In an advantageous embodiment, the pre-processing controller 102 and medical imaging scanner 100 are implemented as part of the same device. The pre-processing controller is implemented by one or more processor executing a set of computer program instructions stored in a storage and loaded into a memory. The pre-processing controller 102 makes determinations of which pre-processing algorithms to apply to a given scan and which parameters of the pre-processing algorithms to use based on a criterion that may be manually configured or automatically determined.

In an advantageous embodiment, the pre-processing controller executes an automatic machine-learning based algorithm to select the pre-processing algorithms to be applied and/or parameters of the pre-processing algorithms. In the machine learning based algorithm, the pre-processing controller receives as input one or more of the following parameters:

A clinical indication for the medical imaging scan;

A purpose for the scan—for example, rule-in a specific disease, rule-out a specific disease or condition, therapy planning, etc.;

Patient-specific data such as height, weight, age, gender, clinical history, comorbidities, etc.;

Scan-specific data such as the kV level, amount of contrast used, collimation settings, etc.;

Other prior imaging studies from the same patient; and/or

Information from the downstream reading/reporting workflow, including:

Availability of automatic image-processing algorithms and their documented performance criterion (e.g., sensitivity and specificity for detection of a particular abnormality; type of input data the available automated image-processing algorithms were trained on; their clinical indication from regulatory approval; etc.); and/or Clinical specialty of the radiologist who will perform the interpretation.

The information regarding which downstream automatic image-processing algorithms are available and the criterion/information associated with the available downstream automatic image processing algorithms can be stored either locally in the storage or memory of the scanner/pre-processing controller device or in a remote database that is accessible to the scanner/pre-processing controller device. The scan-specific data can be directly acquired from the medical imaging scanner 100 by the pre-processing controller 102. The input information including the clinical indication for the scan, the purpose for the scan, the patient-specific data, other prior medical images for the patient, and the clinical specialty of the radiologist who will perform the interpretation of the medical images can be automatically read from an electronic medical record of the patient. For example, such an electronic medical record of the patient containing the input information can be stored in a database of patient electronic medical records, which can be accessed by the pre-processing controller 102 to retrieve the relevant information. Alternatively, some or all of this input information may be manually input by a user (e.g., radiologist).

The pre-processing controller 102 inputs the input parameters into a trained machine learning model, which determines which pre-processing algorithms to perform on the raw data acquired by the medical imaging scanner 100 as well as specific parameters for the pre-processing algorithms. The pre-processing controller 102/machine learning model selects pre-processing algorithms from a set of available possible pre-processing algorithms. This results in a determination of a first set of one or more pre-processing algorithms 104 that generate medical images for visual interpretation by a human 108 and a second set of one or more pre-processing algorithms 106 that generate medical images for processing by automatic image analysis algorithms 110. As shown in FIG. 1, the visual analysis by the human 108 of the medical images generated using the first set of pre-processing algorithms 104 can be combined with the automatic image analysis by the automated artificial intelligence-based image-analysis algorithms 110 of the medical images generated using the second set of pre-processing algorithms 106 to determine the final findings from the medical imaging scan of the patient. Thus, the system of FIG. 1 facilitates joint downstream interpretation of medical imaging scans by humans (e.g., radiologists) and automatic artificial intelligence based image-analysis algorithms.

Figure 2:
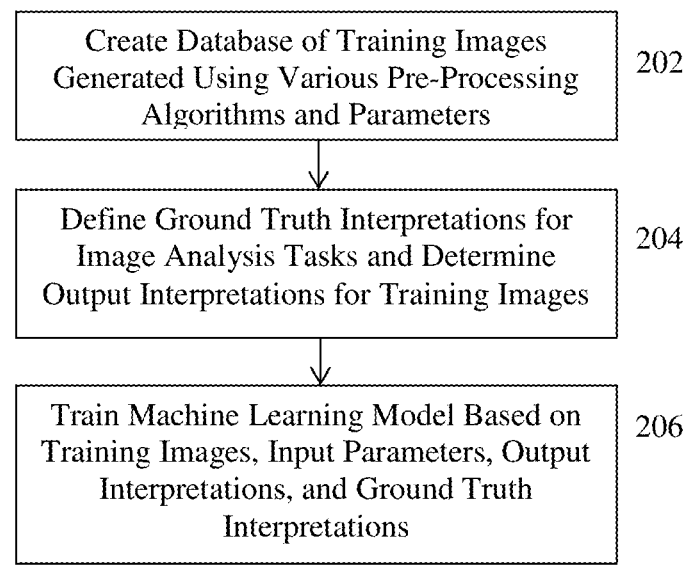
FIG. 2 illustrates a method for training a machine learning model for selecting pre-processing algorithms tailored for possible downstream tasks to be performed on medical images according to an embodiment of the present invention.

FIG. 2 illustrates a method for training a machine learning model for selecting pre-processing algorithms tailored for possible downstream tasks to be performed on medical images according to an embodiment of the present invention. At step 202, a database of training images generated using various pre-processing algorithms and parameters is created. The training database is created that includes medical images that are pre-processed with a variety of pre-processing algorithms (with different partaker settings/parameters), together with known input parameters for each of the training images. The input parameters for each training image may include all or a subset of the input parameters described above that are input to the pre-processing controller.

At step 204, ground truth interpretations are defined for various image analysis tasks and output interpretations are determined for the training images. For each of the training images, output interpretations by one or several radiologists and one or more artificial intelligence (AI) image-analysis algorithms can be determined. Interpretations of a given training image can be performed by one or more radiologists performing relevant image analysis tasks the training image and by performing one or more AI image-analysis algorithms for each image-analysis task relevant to the training image. The ground truth interpretation for each image analysis task is defined to establish an object measure for the results of the image analysis task that can be compared with the output interpretation determined for each image (i.e., the result of performing the image analysis task on a given image using a particular algorithm). The ground truth interpretation for each image analysis task may be defined by majority voting from several different human interpretations and/or AI algorithms for performing the image analysis task, or by a gold standard clinical exam that provides an object optimal result for the image analysis task. For example, in the case of a tumor identification or classification task, the ground truth interpretation can be the findings from a biopsy rather than from the medical image characteristics. In this case, during training, the output interpretation for training images determined using the results of AI algorithms for image-based tumor identification or classification are compared with the ground truth interpretations for the training images determined from biopsies of the corresponding patients. Another example is for image analysis tasks for the assessment of stenosis severity in coronary arteries. Various non-invasive algorithms have been developed for medical image-based assessment of stenosis severity in coronary arteries, including algorithms that use machine learning based techniques and algorithms that use computational fluid dynamics simulations. In this case, the ground-truth interpretation can be an invasive measurement of a hemodynamic metric, such as fractional flow reserve (FFR) or instantaneous wave-free ratio (IFR), rather than the visual or quantitative assessment of the image. During training, output FFR or IFR values for each training image determined using various algorithms for image-based assessment of stenosis severity are compared with the ground truth invasive FFR or IFR values associated with each training image.

At step 206, the machine learning model is trained based on the training images, input parameters, output interpretations determined for the training images, and ground truth interpretations associated with the training images. The machine learning model is trained to map an input medical image and the associated input parameters to a set of algorithms and algorithm settings/parameters to be performed on the medical image. The machine learning model is trained to recognize various downstream medical image analysis tasks and/or AI algorithms to perform those tasks associated with an input medical image based on the medical image and the associated input parameters, and to determine a set of pre-processing algorithms that best suite the downstream image analysis tasks and/or AI algorithms to perform those task. The set of pre-processing algorithms output by the machine learning model can include one or more pre-processing algorithms suited for human visual interpretation of the medical image for one or more image analysis tasks and one or more pre-processing algorithms suited for various AI image analysis algorithms for one or more image analysis tasks. For each task relevant to a given set of training images and each available downstream AI algorithm to perform that task, the machine learning model compares the output interpretations determined for the training images using the AI image analysis algorithm with the ground truth interpretation. Since the training images were pre-processed with various different pre-processing algorithms and settings/parameters, the machine learning model is trained to learn the pre-processing algorithms and settings that provide the most accurate results for the output interpretations as compared to the ground truth interpretations. Thus, the machine learning can learn which pre-processing algorithms and settings are best for various possible downstream AI image-analysis algorithms. In an advantageous embodiment, the machine learning model can be implemented using a deep neural network (DNN) trained using any deep learning algorithms. For example, in a possible implementation, the machine learning model may be a DNN trained using deep reinforcement learning, but the present invention is not limited thereto.

Figure 3:
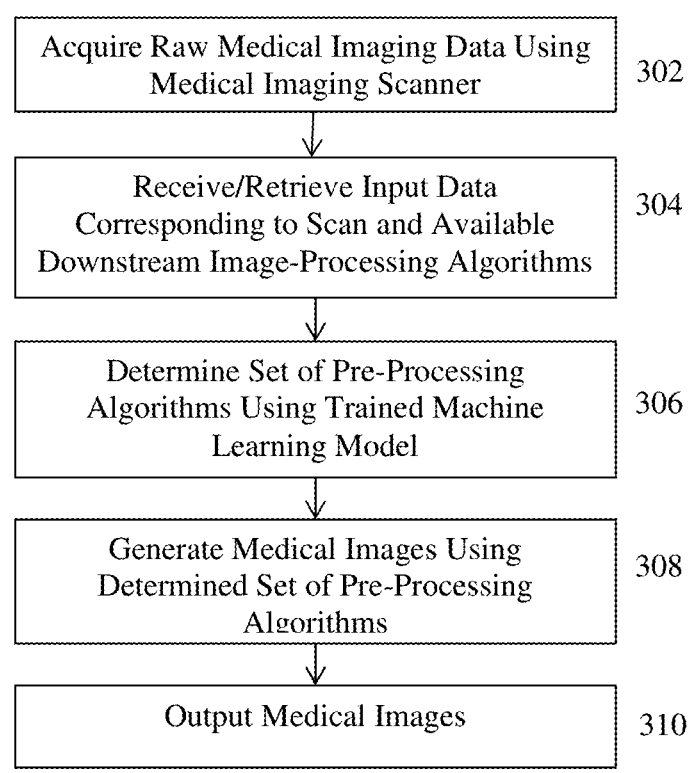
FIG. 3 illustrates a method of medical image pre-processing to facilitate joint interpretation of the medical images by radiologists and artificial intelligence algorithms according to an embodiment of the present invention.

FIG. 3 illustrates a method of medical image pre-processing to facilitate joint interpretation of the medical images by radiologists and artificial intelligence algorithms according to an embodiment of the present invention. In an advantageous embodiment, the method of FIG. 3 is performed by one or more processors at the medical image scanner.

At step 302, raw medical image data is acquired by the medical image scanner. The medical imaging scanner can be a computed tomography (CT) scanner, magnetic resonance (MR) scanner, ultrasound scanner, positron emission tomography (PET) scanner, or any other type of scanner used corresponding to a medical imaging modality. A patient or part of a patient is scanned using the medical image scanner and the medical image scanner acquires raw medical image data representing the anatomy of the patient.

At step 304, input data corresponding to the medical image scan and available downstream image-processing algorithms is received/retrieved. The input data can include one or more of the following parameters related to the scan and the patient: a clinical indication for the medical imaging scan; a purpose for the scan—for example, rule-in specific disease, rule-out a specific disease or condition, therapy planning, etc.; patient-specific data of the patient who is the subject of the scan, such as height, weight, age, gender, clinical history, comorbidities, etc.; scan-specific data such as the kV level, amount of contrast used, collimation settings, etc.; and other prior imaging studies from the same patient. The input data can also include parameters related to the available downstream image-processing algorithms and downstream image processing tasks to be performed, including: information identifying available downstream automatic image-processing algorithms and their documented performance criterion (e.g., sensitivity and specificity for detection of a particular abnormality; type of input data the available automated image-processing algorithms were trained on; their clinical indication from regulatory approval; etc.); and the clinical specialty of the radiologist who will perform the downstream interpretation.

The information regarding which downstream automatic image-processing algorithms are available and the criterion/information associated with the available downstream automatic image processing algorithms can be retrieved either from local storage or memory on the image acquisition device or from remote database. The scan-specific data can be directly acquired from the settings of the medical imaging scanner used to perform the scan of the patient and acquired the raw image data. The input data including the clinical indication for the scan, the purpose for the scan, the patient-specific data, other prior medical images for the patient, and the clinical specialty of the radiologist who will perform the interpretation of the medical images can be automatically read from an electronic medical record of the patient. Alternatively, some or all of this input data may be manually input by a user (e.g., radiologist).

At step 306, a set of pre-processing algorithms for the scan is determined using the trained machine learning model. The trained machine learning model is trained to map the input data associated with the scan to a set of pre-processing algorithms that will generate medical images from the scan that are best suited for the downstream human and AI-based image analysis to be performed on the scan. According to an advantageous embodiment, the trained machine learning model selects a first set of pre-processing algorithms to generate one or more medical images for human visual interpretation and a second set of pre-processing algorithms to generate one or more medical images best suited for one or more automated AI-based image analysis algorithms. The machine learning model may predict a plurality of different automated AI-based image analysis algorithms that are likely to be performed on the scan and the second set of pre-processing algorithms can include respective pre-processing algorithms corresponding to each of the predicted plurality of AI-based image analysis algorithms to generate a respective medical image best suited for each of the predicted AI-based algorithms.

The first set of pre-processing algorithms may include multiple different types of algorithms, such as an image reconstruction algorithm, a filtering algorithm, a de-noising algorithm, etc., that can be used together to generate a resulting medical image best suited for human visual interpretation. It is also possible that the first set of pre-processing algorithms includes multiple different algorithms of the same type (e.g., multiple reconstruction algorithms, multiple filtering algorithms, etc.) or different versions of the same pre-processing algorithm that will result in generating multiple different medical images for suited human visual interpretation. In an advantageous embodiment, the second set of pre-processing algorithms will include a different set of pre-processing algorithms from the first set of pre-processing algorithms. The second set of pre-processing algorithms may include completely different pre-processing algorithms (e.g., for reconstruction, filtering, de-noising, etc.) than the first set of pre-processing algorithms or may include the same algorithms with different settings or parameters. As used herein, the same pre-processing algorithm performed with different parameters is considered two different pre-processing algorithms in the set of pre-processing algorithms. The second set of pre-processing algorithms can include different pre-processing algorithms (or pre-processing algorithms with different settings/parameters) for each predicted AI-based image analysis algorithm. The second set of pre-processing algorithms can include multiple different types of algorithms (e.g., reconstruction, filtering, de-noising, etc.) that can be used together to generate a medical image best suited for each predicted downstream AI-based image analysis algorithm.

Using the trained machine learning model, the knowledge of specific downstream tasks (and associated AI-based algorithms) may be used to set the parameters of a pre-processing algorithm, such as an image reconstruction algorithm. For example, if image segmentation is to be performed on a CT image, then a reconstruction with a sharp kernel may be selected for the automated AI algorithm that performs segmentation, while a reconstruction with a smooth kernel may be used for the medical images that are to be interpreted by the radiologist. In this case, the results for the image segmentation can be displayed on an image that is different from the one that the automated segmentation algorithm analyzed. For example, the results of the segmentation performed on the sharp kernel medical image may be presented to the radiologist on the smooth kernel image.

The trained machine learning model may select different pre-processing algorithms depending on the purpose of the scan. For example, if the clinical indication of the scan is to either rule-in or rule-out a particular disease of findings, the pre-processing controller may be programmed to invoke pre-processing algorithms that are tailored for the particular task, rather than for other image interpretations. By knowing the sensitivity and specificity of the downstream AI algorithm for disease detection, the pre-processing controller can create multiple medical images (by applying different pre-processing algorithms), and obtain a confidence level for the downstream AI algorithm based on the application of the downstream AI algorithm to the multiple medical images. This confidence level can then be presented to the radiologist, or may be used to fuse the results from the radiologist's interpretation with that of the AI algorithm.

At step 308, medical images are generated using the determined set of pre-processing algorithms. The first set of pre-processing algorithms are applied to the raw medical image data acquired by the medical image scanner to generate one or more medical images suited for human visual interpretation (e.g., by a radiologist). The second set of pre-processing algorithms are applied to the raw medical image data acquired by the medical image scanner to generate one or more medical images suited for processing by one or more automated AI-based image analysis algorithms. The second set of pre-processing algorithms may be applied to the raw medical image data to generate a respective medical image for each of a plurality of predicted AI-based image analysis algorithms to be applied.

At step 310, the medical images are output. The medical images generated for human visual interpretation using the first set pre-processing algorithms can be output by displaying the medical images on a display of the image acquisition device or other display device. The medical images generated for one or more various AI-based image analysis algorithms are output to the corresponding AI-base image analysis algorithms. These algorithms can be directly performed by one or more processors of the image acquisition device or the medical images can be output (wirelessly or via a wired connection) to one or more another computer device which is programmed to perform the corresponding AI-based image analysis algorithms. In a possible embodiment, one or more of the medical images generated using the second set of pre-processing algorithms can be transmitted to a cloud-based computer system and the corresponding one or more AI-based image analysis algorithms can be performed as a cloud-based service. It is also possible that medical images generated using the second set of pre-processing algorithms can be displayed on a display of the image acquisition device or another display device. All of the medical images generated using the first and second sets of pre-processing algorithms can also be stored, for example in storage or memory of the image acquisition device or storage or memory of another computer device or remote database.

Once the medical images generated using the second set of pre-processing algorithms are output to the corresponding AI-based image analysis algorithms, the AI-based image analysis algorithms are automatically performed using the corresponding medical images generated for the AI-based image analysis algorithms. For example, such AI-based image analysis algorithms may include, image segmentation algorithms, image registration algorithms, anatomical landmark detection algorithms, disease detection algorithms, image classification algorithms, algorithms to assess the severity of a disease (e.g., stenosis severity), and any other type of automated medical image analysis algorithms. The results of the automated AI-based medical image analysis algorithms can then be displayed on a display device of a computer system (e.g., the image acquisition device or another computer system). In an advantageous embodiment, the results of the automated image analysis performed using one or more AI-based image analysis algorithm can be fused medical image(s) generated for human visual interpretation or fused with the results of the human (radiologist) visual interpretation. In a possible implementation, results of an automated image analysis task performed on a medical image generated using the second set of pre-processing algorithms can be displayed on the medical image generated using the first set of pre-processing algorithms. For example, results of automated image segmentation performed on a medical image generated using reconstruction with a sharp kernel may be presented on a medical image generated using reconstruction with a smooth kernel. In another example, a confidence level for ruling in or ruling out a disease resulting from application of an automated disease detection algorithm on multiple medical images generated using the second set of pre-processing algorithms may be used to fuse the results of the radiologist's interpretation with that of the automated disease detection algorithm.

In a possible further embodiment, the pre-processing controller may have knowledge of the specific software vendor of the downstream AI algorithm, and the machine learning model may be trained to tailor the pre-processing algorithms based on this knowledge, as well as the other input data discussed above. This knowledge may be stored in memory or storage of the image acquisition device, or may be input by a user.

In another possible embodiment, the downstream AI algorithm may have a feedback loop to the pre-processing controller, whereby the downstream AI algorithm may request medical images with multiple specific pre-processing steps applied.

Figure 4:
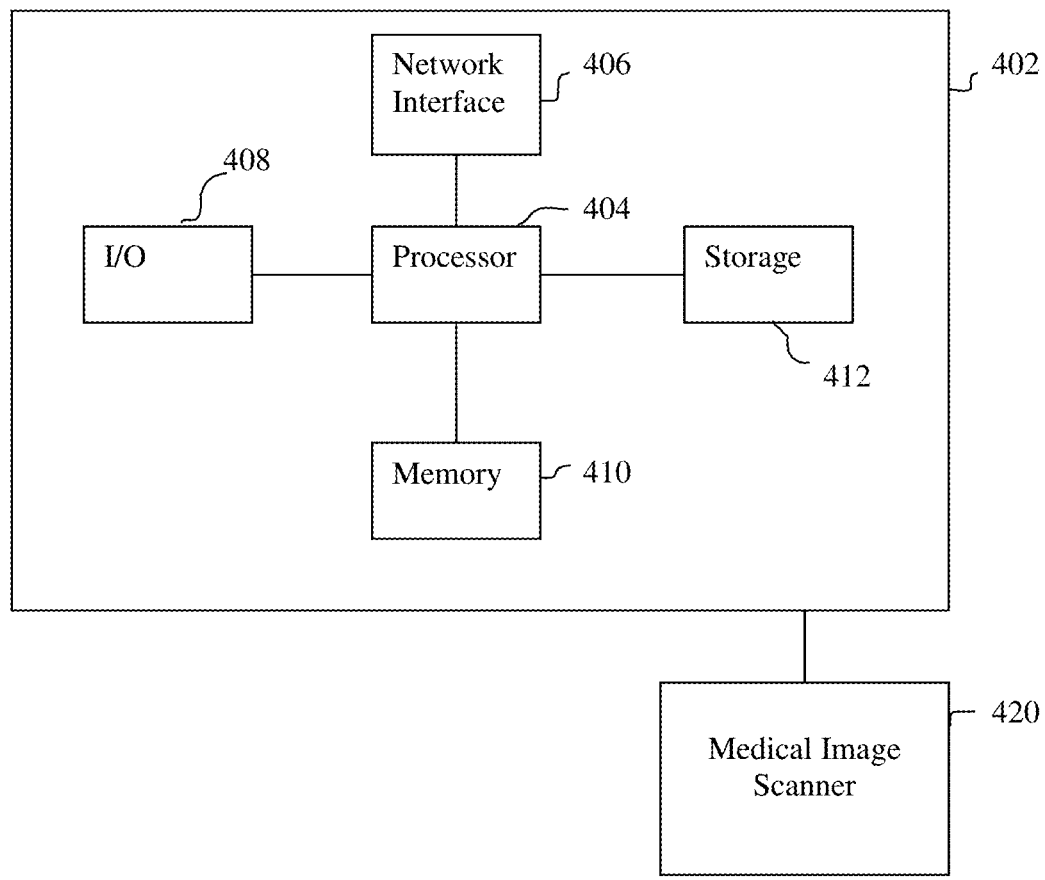
FIG. 4 is a high-level block diagram of a computer capable of implementing the present invention.

The above-described methods can be implemented on one or more computers using computer processors, memory units, storage devices, computer software, and other components. A high-level block diagram of such a computer is illustrated in FIG. 4. Computer 402 contains a processor 404, which controls the overall operation of the computer 402 by executing computer program instructions which define such operation. The computer program instructions may be stored in a storage device 412 (e.g., magnetic disk)

and loaded into memory 410 when execution of the computer program instructions is desired. Thus, the steps of the methods of FIGS. 2 and 3 may be defined by the computer program instructions stored in the memory 410 and/or storage 412 and controlled by the processor 404 executing the computer program instructions. A medical image scanner 420, such as a CT scanning device, X-ray scanning device, C-arm image acquisition device, MR scanning device, Ultrasound device, etc., can be connected to the computer 402 to input image data to the computer 402. In an advantageous embodiment, the medical image scanner 420 and the computer 402 are implemented as one device. It is also possible that the medical image scanner 420 and the computer 402 can be connected by a wired connection or can communicate wirelessly through a network. The computer 402 may also includes one or more network interfaces 406 for communicating with other devices via a network. The computer 402 also includes other input/output devices 408 that enable user interaction with the computer 402 (e.g., display, keyboard, mouse, speakers, buttons, etc.). One skilled in the art will recognize that an implementation of an actual computer could contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for medical image acquisition and pre-processing, comprising:
    acquiring raw medical image data by performing a medical image scan of a patient using a medical image scanner;
    acquiring input data associated with the medical image scan of the patient and available downstream automated image analysis algorithms;
    selecting a set of pre-processing algorithms to apply to the raw medical image data based on the input data associated with the medical image scan of the patient and the available downstream automated image analysis algorithms using a trained machine learning based model, wherein selecting a set of pre-processing algorithms to apply to the raw medical image data based on the input data associated with the medical image scan of the patient and the available downstream automated image analysis algorithms using a trained machine learning based model comprises:
        selecting a first set of one or more pre-processing algorithms for generating one or medical images for human visual interpretation, and
        selecting a second set of one or more pre-processing algorithms for generating one or more medical images for automated image analysis using one or more of the available downstream automated image analysis algorithms; and
    generating one or more medical images from the raw medical image data by applying the selected set of pre-processing algorithms to the raw medical image data, wherein generating one or more medical images from the raw medical image data by applying the selected set of pre-processing algorithms to the raw medical image data comprises:
        generating one or more medical images for human visual interpretation by applying the first set of one or more pre-processing algorithms to the raw medical image data, and
        generating one or more medical images for automated image analysis by applying the second set of pre-processing algorithms to the raw medical image data.

2. The method of claim 1, further comprising:
    displaying the one or more medical images for human visual interpretation generated using the first set of pre-processing algorithms on a display device; and
    providing the one or more medical images for automated image analysis generating using the second set of pre-processing algorithms as input to one or more of the available downstream automated image analysis algorithms.

3. The method of claim 2, further comprising:
    displaying results of the automated image analysis performed on the one or more medical images generated using the second set of pre-processing algorithms by the one or more of the available downstream automated image analysis algorithms on the one or more medical images generated using the first set of pre-processing algorithms.

4. The method of claim 1, wherein the first set of pre-processing algorithms and the second set of pre-processing algorithms include reconstruction algorithms with different settings.

5. The method of claim 1, wherein the second set of pre-processing algorithms includes one or more pre-processing algorithms corresponding to each of a plurality of available downstream automated image analysis algorithms predicted to be applied to the medical image scan, and generating one or more medical images for automated image analysis by applying the second set of pre-processing algorithms to the raw medical image data comprises:
    generating a respective medical image suited for each of the plurality available downstream automated image analysis algorithms predicted to be applied to the medical image scan using the corresponding one or more pre-processing algorithms in the second set of pre-processing algorithms.

6. The method of claim 1, wherein the trained machine learning based model is trained based on a training database of training images acquired using a variety of pre-processing algorithms by comparing output interpretations of the training images determined using one or more available downstream automated image processing algorithms with ground truth interpretations of the training images.

7. An apparatus for medical image acquisition and pre-processing, comprising:
    means for acquiring raw medical image data by performing a medical image scan of a patient using a medical image scanner;
    means for acquiring input data associated with the medical image scan of the patient and available downstream automated image analysis algorithms;
    means for selecting a set of pre-processing algorithms to apply to the raw medical image data based on the input data associated with the medical image scan of the patient and the available downstream automated image analysis algorithms using a trained machine learning based model, wherein the means for selecting a set of pre-processing algorithms to apply to the raw medical image data based on the input data associated with the medical image scan of the patient and the available downstream automated image analysis algorithms using a trained machine learning based model comprises:
  means for selecting a first set of one or more pre-processing algorithms for generating one or medical images for human visual interpretation, and
  means for selecting a second set of one or more pre-processing algorithms for generating one or more medical images for automated image analysis using one or more of the available downstream automated image analysis algorithms; and
means for generating one or more medical images from the raw medical image data by applying the selected set of pre-processing algorithms to the raw medical image data, wherein the means for generating one or more medical images from the raw medical image data by applying the selected set of pre-processing algorithms to the raw medical image data comprises:
  means for generating one or more medical images for human visual interpretation by applying the first set of one or more pre-processing algorithms to the raw medical image data, and
  means for generating one or more medical images for automated image analysis by applying the second set of pre-processing algorithms to the raw medical image data.

8. The apparatus of claim 7, further comprising:
means for displaying the one or more medical images for human visual interpretation generated using the first set of pre-processing algorithms on a display device; and
means for providing the one or more medical images for automated image analysis generating using the second set of pre-processing algorithms as input to one or more of the available downstream automated image analysis algorithms.

9. The apparatus of claim 7, wherein the second set of pre-processing algorithms includes one or more pre-processing algorithms corresponding to each of a plurality of available downstream automated image analysis algorithms predicted to be applied to the medical image scan, and the means for generating one or more medical images for automated image analysis by applying the second set of pre-processing algorithms to the raw medical image data comprises:
  means for generating a respective medical image suited for each of the plurality available downstream automated image analysis algorithms predicted to be applied to the medical image scan using the corresponding one or more pre-processing algorithms in the second set of pre-processing algorithms.

10. The apparatus of claim 7, wherein the trained machine learning based model is trained based on a training database of training images acquired using a variety of pre-processing algorithms by comparing output interpretations of the training images determined using one or more available downstream automated image processing algorithms with ground truth interpretations of the training images.

11. A non-transitory computer readable medium storing computer program instructions for medical image acquisition and pre-processing, the computer program instructions when executed by a processor cause the processor to perform operations comprising:
  acquiring raw medical image data by controlling a medical image scanner to perform a medical image scan of a patient;
  acquiring input data associated with the medical image scan of the patient and available downstream automated image analysis algorithms;
  selecting a set of pre-processing algorithms to apply to the raw medical image data based on the input data associated with the medical image scan of the patient and the available downstream automated image analysis algorithms using a trained machine learning based model, wherein selecting a set of pre-processing algorithms to apply to the raw medical image data based on the input data associated with the medical image scan of the patient and the available downstream automated image analysis algorithms using a trained machine learning based model comprises:
    selecting a first set of one or more pre-processing algorithms for generating one or medical images for human visual interpretation, and
    selecting a second set of one or more pre-processing algorithms for generating one or more medical images for automated image analysis using one or more of the available downstream automated image analysis algorithms; and
  generating one or more medical images from the raw medical image data by applying the selected set of pre-processing algorithms to the raw medical image data, wherein generating one or more medical images from the raw medical image data by applying the selected set of pre-processing algorithms to the raw medical image data comprises:
    generating one or more medical images for human visual interpretation by applying the first set of one or more pre-processing algorithms to the raw medical image data, and
    generating one or more medical images for automated image analysis by applying the second set of pre-processing algorithms to the raw medical image data.

12. The non-transitory computer readable medium of claim 11, further comprising:
displaying the one or more medical images for human visual interpretation generated using the first set of pre-processing algorithms on a display device; and
providing the one or more medical images for automated image analysis generating using the second set of pre-processing algorithms as input to one or more of the available downstream automated image analysis algorithms.

13. The non-transitory computer readable medium of claim 11, wherein the second set of pre-processing algorithms includes one or more pre-processing algorithms corresponding to each of a plurality of available downstream automated image analysis algorithms predicted to be applied to the medical image scan, and generating one or more medical images for automated image analysis by applying the second set of pre-processing algorithms to the raw medical image data comprises:
  generating a respective medical image suited for each of the plurality available downstream automated image analysis algorithms predicted to be applied to the medical image scan using the corresponding one or more pre-processing algorithms in the second set of pre-processing algorithms.

14. The non-transitory computer readable medium of claim 11, wherein the trained machine learning based model is trained based on a training database of training images acquired using a variety of pre-processing algorithms by comparing output interpretations of the training images determined using one or more available downstream automated image processing algorithms with ground truth interpretations of the training images.

\* \* \* \* \*